(12) United States Patent
Von Behren et al.

(10) Patent No.: US 6,824,518 B2
(45) Date of Patent: Nov. 30, 2004

(54) HIGH TRANSMIT POWER DIAGNOSTIC ULTRASOUND IMAGING

(75) Inventors: Patrick L. Von Behren, Bellevue, WA (US); Alampallam R. Ramachandran, Sammamish, WA (US); Zoran B. Banjanin, New Castle, WA (US); Wayne J. Gueck, Redmond, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 10/304,350

(22) Filed: Nov. 26, 2002

(65) Prior Publication Data

US 2004/0102703 A1 May 27, 2004

(51) Int. Cl.[7] ................................................. A61B 8/00
(52) U.S. Cl. ........................................................ 600/443
(58) Field of Search ................................ 600/437, 439, 600/443, 447, 454–456, 458; 601/2–4

(56) References Cited

U.S. PATENT DOCUMENTS

| | | | |
|---|---|---|---|
| 4,796,632 A | | 1/1989 | Boyd et al. |
| 5,435,311 A | * | 7/1995 | Umemura et al. .......... 600/439 |
| 5,487,387 A | | 1/1996 | Trahey et al. |
| 5,556,372 A | * | 9/1996 | Talish et al. .................... 601/2 |
| 5,558,092 A | * | 9/1996 | Unger et al. ................ 600/439 |
| 5,657,760 A | * | 8/1997 | Ying et al. ................... 600/439 |
| 5,694,937 A | | 12/1997 | Kamiyama |
| 5,769,790 A | * | 6/1998 | Watkins et al. ............. 600/439 |
| 5,833,613 A | | 11/1998 | Averkiou et al. |
| 5,846,202 A | | 12/1998 | Ramamurthy et al. |
| 5,860,928 A | | 1/1999 | Wong et al. |
| 5,957,845 A | | 9/1999 | Holley et al. |
| 6,042,556 A | * | 3/2000 | Beach et al. .................... 601/3 |
| 6,086,535 A | * | 7/2000 | Ishibashi et al. ............ 600/439 |
| 6,110,120 A | | 8/2000 | Holley et al. |
| 6,210,335 B1 | | 4/2001 | Miller |

(List continued on next page.)

OTHER PUBLICATIONS

"Thermal Dose Determination in Cancer Therapy," by Stephen A. Sapareto, Ph.D. and William C. Dewey, Ph.D.; Int. J. Radiation Oncology—Biology—Physics; vol. 10, No. 6, pp. 787–800; Jun. 1984.

(List continued on next page.)

*Primary Examiner*—Francis J. Jaworski

(57) ABSTRACT

Methods and systems for improving an ultrasound image quality are provided. On demand transmission of unsustainably high power ultrasonic pulses are temporary or spatially interleaved with low power, zero power, or standard ultrasonic pulses. In response to a user initiated trigger, a physiological trigger, a system trigger, or external equipment trigger, the unsustainably high power pulses provide better signal-to-noise ratio and/or allow increased imaging frequencies for difficult to image patients in any of various modes, such as B-modes, harmonic B-mode responsive to tissue or contrast agent, or color flow modes. Unsustainably high power ultrasonic pulses cause an increase in the tissue temperature within the body and at the interface between the transducer and the skin. Standard imagining or standard high power pulses may increase either temperature by around 6° C., such as from a body normal 37° C. to an average of 43° C. over time. The unsustainably high power ultrasonic pulses may cause the temperature to exceed 43° C. for a limited time period. For example, the in-situ temperature may be increased to 50° C. for one second, but the temperature is not sustained at this level. Tissue damage may occur for increased temperature over a long period of time, unlike the standard 43° C. for ultrasound imaging. A thermocouple or/and software for temperature and procedure monitoring prevent operator errors in causing harm to patient and/or transducer.

45 Claims, 2 Drawing Sheets

U.S. PATENT DOCUMENTS

| | | | |
|---|---|---|---|
| 6,306,095 B1 | | 10/2001 | Holley et al. |
| 6,334,846 B1 | * | 1/2002 | Ishibashi et al. ............ 600/439 |
| 6,340,348 B1 | | 1/2002 | Krishnan et al. |
| 6,371,912 B1 | | 4/2002 | Nightingale et al. |
| 6,374,674 B1 | | 4/2002 | Mine |
| 6,425,867 B1 | * | 7/2002 | Vaezy et al. ................ 600/439 |
| 6,428,477 B1 | * | 8/2002 | Mason ....................... 600/437 |

OTHER PUBLICATIONS

"Arrhenius Relationships From the Molecule and Cell to the Clinic," by W. C. Dewey; International Journal of Hyperthermia; vol. 10, No. 5, pp. 457–483, 1994.

* cited by examiner

HIGH TRANSMIT POWER DIAGNOSTIC ULTRASOUND IMAGING

BACKGROUND

The present invention relates to ultrasound imaging. In particular, ultrasound imaging using increased transmit powers is provided.

In U.S. Pat. Nos. 5,957,847, 6,110,120, and 6,306,095, contrast agent imaging uses two different transmit power levels. Contrast agent microspheres are destroyed by standard ultrasound imaging power levels, such as B-mode imaging transmissions. The standard transmit powers are adapted to avoid violation of current limitations on transmit power, such as mechanical index and thermal indices. Loss of correlation due to the destruction of contrast agents may provide for high contrast images. However, to allow contrast agents to build up, transmit levels are reduced from standard transmit levels between higher power transmissions. The reduced transmit levels provide images while minimizing destruction of the contrast agent.

Increased transmit voltage or pulse length may be provided for cardiac applications, such as shown in U.S. Pat. No. 6,210,335, the disclosure of which is incorporated herein by reference. The imaging frame rate is reduced to allow an increase in transmit power within current FDA (Food And Drug Administration) and IEC (International Electrotechnical Commission) limits of mechanical index, thermal index, and transducer temperature. In response to a trigger, one or two frames of data associated with the increased transmit voltage or pulse length are acquired. The resulting images may have an increased color flow sensitivity or deeper penetration. However, the reduction in frame rate may be undesirable in some situations.

U.S. Pat. No. 5,487,387 discloses transmitting high intensity acoustic energy to initiate acoustic streaming of fluids within a region, and U.S. Pat. No. 6,371,912 discloses transmitting high intensity acoustic energy to initiate palpation of tissue, also called ARFI (acoustic radiation force imaging). Receive signals responsive to the high intensity signals are used to detect the acoustically induced movement or streaming of fluid. Acoustically induced movement of tissue may be detected as well.

BRIEF SUMMARY

The present invention is defined by the following claims, and nothing in this section should be taken as a limitation on those claims. By way of introduction, the preferred embodiments described below include methods and systems for improving ultrasound image quality. On demand transmission of unsustainably high power ultrasonic pulses is temporally or spatially interleaved with sustainable low power, zero power, or standard ultrasonic pulses. The duration of the unsustainably high power ultrasonic pulses is a function of a time-tissue temperature relationship. Unsustainably high power pulses provide better penetration, improve signal-to-noise ratio and allow higher imaging frequencies for difficult to image patients in any of various modes, such as B-mode, harmonic B-mode responsive to tissue, contrast agent modes, color flow modes, M-mode, mixed modes, or other modes. These features are especially desirable for difficult-to-image patients, where body habitus makes satisfactory image quality problematic.

Sustainable transmit power is defined as that which can be employed indefinitely for imaging. Its upper bound is limited by system power delivery capability, transducer temperature, skin temperature, internal tissue temperature and peak rarefactional pressure. The various temperatures reach equilibrium values and are assumed to be maintained for the duration of the ultrasound imaging diagnostic procedure. Regulatory temperature limits are set so as to not cause thermal damage to the patient.

Further aspects and advantages of the invention are discussed below in conjunction with preferred embodiments.

BRIEF DESCRIPTION OF SEVERAL VIEWS OF THE DRAWINGS

The components and the figures are not necessary to scale. Emphasis instead being placed upon illustrating the principles of the invention. Moreover, in the figures, like reference numerals designate corresponding parts through the different views.

DETAILED DESCRIPTION OF THE PREFERRED EMBODIMENTS

Figure 1:
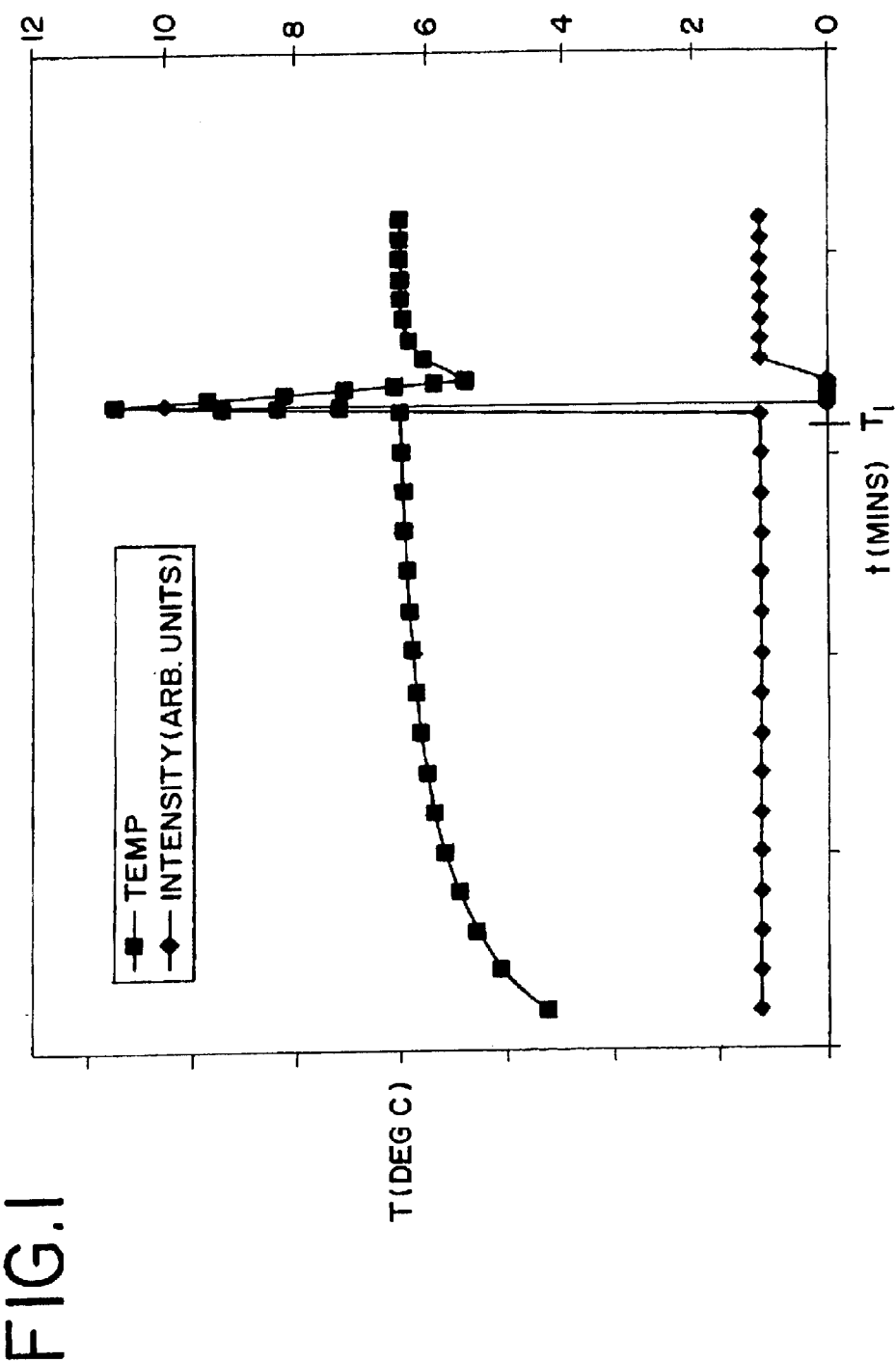
FIG. 1 is a graphical representation showing temperature and intensity or power as a function of time in one embodiment of unsustainable imaging.

Unsustainable transmit power is that which is not sustainable. Sustainable transmit power is defined as that which can be employed indefinitely for imaging. The upper bound of sustainable transmit power is limited by system transmit voltage and power delivery capacity, is also limited by the mechanical index that is related to the in-vivo peak rarefactional acoustic pressure and is a measure of the level of mechanical bio-effects produced in the body. The sustainable transmit power is also limited by thermal bio-effects considerations relating to tissue heating that limit the average acoustic intensity transmitted into the body as well as the temperature of the transducer surface in contact with the patient's skin. In this case, the skin and internal tissue temperatures are equilibrium or steady state values attained due to the sustained application of ultrasound power for time periods that are larger than the time required for equilibrium conditions to be created or measured. Conventionally, the consideration of thermal bio-effects does not limit the time periods over which power levels may be sustained, at least to any time less than the length of an ultrasound exam. The IEC limits the steady state transducer surface temperature to 43° C. The FDA requires justification if any thermal index exceeds 6, that is if the estimated internal tissue temperature exceeds 43° C.

Unsustainable transmit power is that which is not sustainable. A thermal dose applied to tissue is a function of both the tissue temperature and the time for which the tissue is at that temperature. Thermal dose is measured in terms of equivalent time at a reference temperature, typically 43° C. Thermal dose is defined by the following equation:

$$t_{43} = \int F(T(t))dt$$

where, $f(T(t)) = 0.5^{(43-T)}$ for 43° C. > T $f(T(t)) = 0.25^{43-T}$ for 40° C. < T ≤ 43° C.

where $f$ is a function of temperature, T, which is a function of time, t. This equation implies tissue damage is faster at higher temperatures and has been verified down to 1 second and 57° C. Thermal exposure time periods at different temperatures may be reduced to an equivalent time period at the reference temperature, such equivalence implying equivalent tissue damage. A safe and acceptable tissue specific equivalent time at 43° C., $t_{43}$, is a limit that may not be exceeded.

When considering thermal bio-effects, a more general way to define the transmit power limit is that based upon a consideration of the thermal dose applied to skin or other internal tissue. In order to limit the damage to negligible or acceptable levels, the time duration over which a certain transmit power is used may be limited (i.e. the transmit power level is unsustainable). This duration for the thermal or other dose is continuous or includes time periods separated by one or more temporal gaps (e.g. transmitting unsustainable pulses in different sets with no or sustainable transmissions in between or transmitting two or more unsustainable pulses with a period of no transmission or transmission of other pulse(s) in between each or groups of unsustainable pulses. The transmit power and time duration limit combination are not fully based upon a linear average of the instantaneous intensities over time. A non-linear relationship between the transmit power and the time duration is used, such as an exponential or other nonlinear time-tissue temperature relationship. For example if a certain safe $t_{43}$ value is 16 minutes, then the above equation would indicate that the tissue may be heated to 44° C. for 8 minutes or 47° C. for 1 minute. The nonlinear relationship between the allowed time period and the temperature is $t_{allowed} = t_{43} * 2^{(43-T)}$ for a given tissue specific $t_{43}$ and fixed temperature above 43° C. The exposure time thus may be controlled for a range of temperatures say, between 43° C. and 50° C. using the above non-linear relationship with temperature.

Other non-linear relationships between transmit power and duration may be used. Sustainable transmit powers allow for durations covering at least an ultrasound examination (e.g. 10–15 minutes). Unsustainable transmit powers allow for increased transmit power, but at a lesser duration. The power dose is a function of the power transmitted and the duration of transmission. The duration is set less than the maximum thermal or power dose that avoids unacceptable tissue damage.

High power, unsustainable ultrasonic pulses are employed to improve diagnostic ultrasound images. High power, unsustainable ultrasonic pulses may be interleaved with lower power ultrasonic pulses. For example, unsustainably high power pulses are transmitted for a short period of time, and then lower power, sustainable imaging or a short period of no transmission followed by lower power, sustainable imaging is resumed. Unsustainable high power transmission and responsive images may cause an increase in temperature of internal tissue as well as on the skin surface, but provides for improved imaging quality in hard to image patients, such as patients with above normal layers of fatty tissue.

Power is increased by increasing the length or amplitude of the transmit waveform, pulse repetition frequency or other characteristic increasing the amount of power transmitted into a patient. Thermal dose may be used to limit the duration of time that unsustainably high transmit powers may be used, such as imaging for 32 seconds at 47° C., 8 seconds at 49° C. or 2 seconds at 51° C. Unsustainably high power transmissions may improve diagnostic capabilities by providing deeper penetration and/or better spatial resolution through higher frequency imaging to the same depth. The improved images or other data may be stored for later review, such as by persisting or replaying the images on the display during the period of no transmissions. In addition to improving the quality of an image, the high power pulses may be applied to other operational modes such as acoustic streaming, acoustic radiation force imaging, contrast imaging, drug delivery through increased temperature, or therapeutic applications.

FDA, IEC or other regulations either limit or require justification for the transducer surface temperature, in-situ average spatial peak intensity (ISPTA), acoustic mechanical index (MI), and acoustic thermal index (TI) during ultrasound imaging. These regulations result in limits on the transmit voltage, pulse repetition frequency, number of cycles of a transmit waveform and the line density or spatial distribution of the acoustic energy.

MI is an instantaneous value directly related to the peak rarefactional pressure. Where the mechanical index limits an increase of transmit voltage, other parameters, such as the pulse length, may be altered to increase the transmit power. Since MI is proportional inversely to the square root of the signal frequency, the transmit frequency may be increased with a simultaneous increase in voltage without exceeding the MI but providing an improved or higher resolution image.

The transducer temperature regulation is a steady state value measured or estimated after the ultrasound system has been in continuous operation for a time period in a sustainable operating condition. The transducer surface temperature is limited to 43° C. by the IEC. To achieve compliance with transducer heating regulations, the transducer surface temperature should not exceed 43° C. at the end of the 30 minutes of continuous transmission into a tissue-mimicking target. Another test requires that the surface temperature not exceed 50° C. after 30 minutes of continuous operation when the transducer is held in still air. Due to the time constant associated with the thermal mass and heat flow in a typical transducer, the temperature rises exponentially and reaches a steady state and limiting value given a constant generation of acoustic energy. In alternative embodiments, other nonlinear relationships between time and tissue or transducer temperature are used to determine the duration. The temperature rise depends on the power output by the transducer, so depends on transmit parameters such as the transmit voltage, pulse length, pulse repetition frequency, and transmit line density. During a short period of unsustainable high power transmit pulses, the slow temperature reaction due to the time dependence of the transducer heating allows for improved imaging while possibly exceeding the 43° C. limit for a limited time. By returning to standard or sustainable transmit powers for a period of time, the transducer also returns to lower, sustainable temperatures.

TI is also a steady state value like the transducer temperature. The ISPTA is an average value over a characteristic time period of a repetitive pulse sequence. The ISPTA is limited because of the potential for in-vivo tissue damage due to heating and so is linked to the TI. The FDA limits ISPTA to 0.72 W/cm$^2$. The thermal indexes (TIS, TIB, and TIC) are typically expected to be below six, implying that the in-vivo temperature is limited to 43° C. to avoid thermally induced tissue damage. Higher TI values require justification.

The ISPTA and TI regulations may be altered to allow for unsustainably high power transmissions for a short time period. Since in-vivo heating processes have characteristic time constants, a higher transmit power can be used for a short time, such that the temperature rise is below 43° C. or if higher, the time duration at the higher temperature does not lead to thermally induced damage. If higher transmit powers are used for time periods that are small in comparison with the time constant associated with transducer and tissue heating, the temperature rise may be limited and allowed without tissue damage. Taking advantage of the time constant for temperature response, increased voltage, pulse length, pulse repetition frequency, aperture and/or other power and temperature increasing characteristics may be used for short time periods.

FIG. 1 shows a temperature profile of transducer heating in conjunction with the transmitted intensity or power as a function of time. In-situ temperature response may be similar. During an initial period to time $T_1$, the transmit power is provided at a sustainable power level, such as resulting in a temperature at or below 43° C. during continuous imaging. After time $T_1$, the power is increased, such as by a factor of 10, for a short time, such as six seconds. As a result of the increased transmit power, the temperature rises above the steady state in $T_1$ to an unsustainably high level. To avoid tissue damage, the unsustainably high transmit power ends, and no or lower power pulses are transmitted. In the embodiment shown in FIG. 1, no transmit pulses are used for a time period after the unsustainably high transmit pulses, such as not transmitting for a 45 second time period. As a result, the temperature exceeds 43° C. for only a short time period, avoiding in-situ tissue damage or damage to the patient's skin. The system then resumes imaging at the sustainable transmit power. By increasing the transmit power by a factor of 10, about a 10 dB improvement in image signal-to-noise ratio and a penetration depth increase results.

With some ultrasound transducers, a large percentage of B-mode and B-mode and color or Doppler mode combination imaging are limited by transducer temperature. Where the limits on mechanical index, TI and in-vivo intensity do not constrain the transmit power, the unsustainably high transmit power is based on the transducer temperature. Alternately, the unsustainably high transmit power is based on the TI or in-vivo intensity. Where tissue damage is avoided or insignificant, regulations may be altered to allow for use of unsustainably high transmit powers for some period of time.

Thermal damage of tissue is a chemical process involving activation energy and follows an Arrhenius time-temperature relationship (Sapareto SA & Dewey WC (1984) Int. J. Rad. Oncol. Biol. Phys 10 787–800 Thermal dose determination in cancer therapy, and Dewey WC (1994) Int. J. Hyperthermia 10 457–483 Arrhenius relationships from the molecule and cell to the clinic). Damage occurs at a rate that is faster at higher temperatures. Empirical studies indicate that a shorter time at a higher temperature is equivalent to a longer time at a lower temperature in terms of the extent of tissue damage. As a result, thermal dose may be measured in units of time at a reference temperature. Using 43° C. as a reference, the equivalent time, $t_{43}$ is provided by $t_{43} = \Sigma f(T(t)) \Delta t$, where $f(T(t)) = 0.25^{43-T}$ at $40 < T \leq 43$, and $= 0.50^{43-T}$ at $T > 43$; $\Delta t$ represents a time interval. For any tissue type, the limit on temperature rise and time duration can be determined once the value of $t_{43}$ resulting in measurable damage is known.

Figure 2:
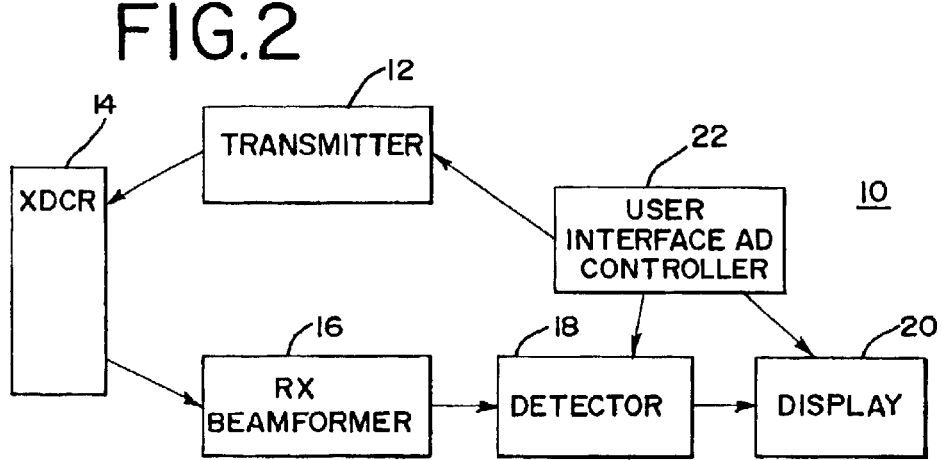
FIG. 2 is a block diagram of one embodiment of a system for improving ultrasound image quality.

FIG. 2 shows an ultrasound system 10 of one embodiment for improving ultrasound image quality. The system 10 includes a transmitter 12, a transducer 14, a receive beamformer 16, a detector 18, a display 20 and a user interface and controller 22. Additional, different or fewer components may be provided.

The user interface and controller 22 comprises a keyboard, dedicated buttons, track ball, a mouse, a joystick, programmable buttons, dials, slides, or other now known or later developed devices for inputting information into the ultrasound system 10. The user interface and controller 22 also includes one or more of processors, such as general processor, digital signal processor, application specific integrated circuit, other digital device, memory or analog device for controlling the components in the system 10 in response to input from the user.

The user interface controller 22 is operable to make unsustainable imaging, (i.e., imaging using transmit power at an unsustainable level), available for one or more modes of imaging. In one embodiment, imaging using unsustainably high transmit powers is available for 2,3, or more modes, such as being available for any mode of imaging. For example, the user is provided with a selection for unsustainably high transmit powers as part of a set up of a particular mode of imaging. As another example, the user configures the system 10 to use an unsustainably high transmit power and is provided with a list of different modes of imaging available for use with the increased transmit powers. As yet another example, user initiation with a dedicated or other input activates unsustainably high transmit powers during standard or conventional imagining in any of various modes. In one embodiment, at least one of the modes usable with unsustainably high transmit powers is other than a color flow or Doppler mode. Imaging modes usable with the unsustainably high transmit power include B-mode, Doppler mode, color flow mode, harmonic imaging, harmonic imaging of contrast agents, harmonic imaging free of contrast agents within the image region during an entire imaging session, M-mode, mixed modes, interleaved modes, three-dimensional imaging modes, four-dimensional imaging modes, extended field of view imaging modes, acoustic streaming, ARFI (acoustic radiation force imaging), strain imaging, strain rate imaging, stress echo imaging, combinations thereof, or any other imaging mode now known or later developed for ultrasound systems.

As described above, unsustainably high transmit powers include transmit powers that result in thermal dose or transmit power conditions not sustainable over a long time period or not sustainable for continuous imaging. If the power levels are unsustainable, for example, the transmitter 12 may over heat and fail. The transducer 14 may over heat and fail or harm tissue, or internal tissue damage may result due to the acoustic energies. Sustainable powers avoid temperature damage over a longer time period, such as a time period associated with an imaging session for a given patient or for a given mode. Imaging sessions typically last between a quarter hour and a half hour and involve using the ultrasound system for one or two diagnostic procedures. The unsustainable high transmit powers last for a period less than the imaging session, such as a period of milliseconds, seconds, or minutes.

By making unsustainably high transmit powers available for any of various imaging modes, improved diagnostic ultrasound images are provided for many different applications or conditions. Increased penetration depth, increased resolution, better flow sensitivity, improved signal-to-noise ratio, and/or other image improvements are provided without sacrifices to frame rate, line density, or other parameters that may provide less desirable imaging characteristics. For example in high mechanical index contrast agent imaging using B-mode or loss of correlation detection, higher transmit intensities may provide for a more complete destruction of contrast agent, better identifying regions associated with tissue and flow. Higher intensities may also provide for more efficient drug delivery while also imaging, such as increasing drug up-take through an increase in temperature and controlling position with B-mode or any mode of imaging. As another example, harmonic B-mode imaging of tissue free of contrast agent throughout an entire imaging session with unsustainably high transmit powers may provide better generation of harmonic information through propagation, resulting in better signal-to-noise ratio in high resolution harmonic images. As yet another example, volume frames or frames of data representing three dimensional space with high signal-to-noise ratio may be acquired and stored for three dimensional imaging with a mechanically rotating array or other transducer array.

In one alternative embodiment, unsustainably high transmit powers may be used without imaging as well, such as using unsustainable pulses for destruction of contrast agent, ARFI or other transmissions for interacting with structure or fluid without receiving or imaging from directly responsive echoes. Sustainable pulses are used for imaging (e.g. transmit sustainable pulses and receive responsive echoes to generate an image). The images are free of echoes directly responsive to the transmission of unsustainable pulses. Directly is used to allow for reverberation or reflections from deep tissue or fluid responsive to the unsustainable pulses during transmission and reception of sustainable pulses. Alternatively, additional or different unsustainable pulses are used for imaging.

Unsustainably high transmit powers are provided by increasing the number of cycles in one embodiment, so coded excitation may more likely be used. Longer coded excitation signals for better isolation of desired information through coding may be provided. For acoustic streaming due to acoustic energy as disclosed in U.S. Pat. No. 5,487,387, the disclosure of which is incorporated herein by reference, greater efficiency in the exam is provided by interacting with thicker fluids within a cyst. By timing the application of unsustainably high transmit powers based on temperature, greater efficiency for acoustic streaming is provided.

In response to configuration of the system 10 for use of unsustainably high transmit power or imaging, the user interface and controller 22 optimizes the parameters for the high power transmission. For example, the parameters discussed herein for increasing the transmit power are adjusted. The penetration depth, the frequency, or other parameter adjustable on an ultrasound system 10 also may be adjusted for use of the unsustainably high transmit power. The optimization of the parameters for unsustainably high transmit power imaging is determined as a function of the application, mode of imaging, or patient characteristic. The user interface and controller 22 automatically optimizes the parameters, such as in response to an on-demand initiation by depressing a button, but manual or user controlled optimization may be provided by allowing the user to configure the parameters or adjust the parameters in real time or prior to initiation of the unsustainably high transmit power.

The transmitter 12 comprises a transmit beamformer, waveform generator, digital-to-analog converter, oscillator, transistor network or other digital or analog components for providing electrical signals to the transducer 14. In one embodiment, the transmitter 12 comprises a plurality of channels with waveform generators responsive to timed initiation signals and amplifiers for applying relative delays and/or apodizations to focus one or more scan lines. The transmitter 12 sequentially generates a plurality of beams of acoustic energy within a region to scan a patient. Alternatively, the transmitter generates one or more signals to form a plane wave or a plurality of simultaneous beams.

The transmitter 12 is operable to generate ultrasonic pulses having an unsustainable power. The power is unsustainable as a function of the temperature, such as a temperature of components of the transmitter 12, of the transducer 14 or of tissue. A power source, transformer, amplifier or capacitor for generating high transmit voltages allows for unsustainably high transmit powers through increased amplitudes. The components of the transmitter 12 are operable to function over a long duration, such as associated with 10–10,000 cycles for increasing transmit power by an increased number of cycles within a waveform. Durations for many imaging modes are preferably shorter, in the 10–100 cycle range, while longer durations associated with thousands of cycles may be utilized, in particular for pushing, as in streaming or palpation applications. The transmitter 12 is operable to increase a line density, pulse repetition frequency, or F-number for increasing the transmit power, such as by using memories with sufficient speed, amplifiers, transistors, filters, and other digital or analog components operable to provide the changed parameters for at least the duration of the unsustainably high transmit power. The transmitter 12 is responsive to the user interface controller 22 for selection of the unsustainable imaging for one or more of the various modes. Transmitter 12 is operable to generate transmit waveforms with a higher frequency for better resolution using unsustainable transmit powers, such as by using clock speeds and analog and digital components operable at the increased frequencies (e.g. 1–20 MHz).

The transmitter 12 is also operable to generate ultrasonic pulses having sustainable power, such as lower power pulses sustainable without damage due to temperature throughout an imaging session. For example, conventional power transmit pulses are generated with amplitude amplifiers. In one embodiment, the transmitter 12 is operable to generate lower power transmit pulses for allowing a more rapid decrease in tissue temperature, such as pulses resulting in a steady state temperature below 43° C.

The transducer 14 comprises one or more elements of piezoelectric material or microelectromechanical devices. In one embodiment, the transducer 14 comprises a one-dimensional, 1.25 D, 1.5 D, 1.75 D, or 2 dimensional array of elements. The transducer 14 connects with the transmitter 12 to receive transmit electrical waveforms for each element within a transmit aperture. The transducer 14 generates acoustic waveforms responsive to the electrical waveforms for transmitting a plane wave or one or more simultaneous focused beams of acoustic energy. The transducer 14 is also operable to receive echoes responsive to the transmitted acoustic energy and provide electrical signals representing the echoes for each element within a receive aperture to the receive beamformer 16.

The transducer 14 comprises a conventional transducer with ceramic and epoxy material in one embodiment. In an alternative embodiment, one or more devices for influencing the temperature at the skin surface, the transducer heating constant, or transducer heating are provided. For example, a copper or other metallic conductor transfers heat away from the transducer. Other cooling techniques may be used, such as active cooling with heat pumping and/or thermoelectric devices or transfer of heat to fluid moving through the transducer.

In yet another alternative, passive isolation from short time temperature rises is provided by adding a standoff to the face of the transducer 14. The standoff spaces the transducer 14 away from the skin and acts as a heat insulator. For example, the rubber, epoxy or plastic window of a transducer is thickened to provide more heat insulation. As another example, TPX or other plastic connects in front of the window. The standoff allows the use of even higher transmit powers during short time periods of operation due to the insulation. The standoff may increase the thermal mass as well as acting as an insulator. U.S. Pat. No. 4,796,632, the disclosure of which is incorporated herein by reference, discloses physical structures of possible standoffs that are connectable with the transducer 14, but other connectable or permanent standoffs may be provided. U.S. Pat. No. 4,796,632 lists use of standoff as way of improving near field imaging, where in this disclosure, the standoff is used as an insulator.

The receive beamformer 16 comprises one or more amplifiers and delays in a plurality of channels for connecting with a respective plurality of elements of the transducer 14. After applying apodization and/or delays for each channel relative to other channels, a summer of the received beamformer 16 generates in-phase and quadrature or radio frequency (RF) information representing a spatial location within a scanned region. The apodization and/or delay profiles change as a function of depth. The receive beamformer 16 may also include a filter for isolating information at a particular frequency, such as a fundamental transmit frequency, a second harmonic of the fundamental transmit frequency or other harmonic frequency bands.

In one embodiment, a memory, such as a random access memory, hard drive, diskette, tape, or other memory, records the raw unprocessed data at an output of the receive beamformer 16. The memory stores frames of data responsive to the unsustainably high transmit powers. By providing a memory for the receive beamformer output, versatility is provided for subsequently generating images from the stored data. The signals from the transducer 14 for each element may be stored in alternative embodiments, or a later CINE memory provided after the detector 18 may be used. The user adjusts any of various parameters, such as an overall gain, spatial filtering or temporal filtering for generating an image from the stored data. Alternatively, the image is generated in real time from acquired data without storage in the memory.

The detector 18 comprises one or more of a B-mode detector, a color flow detector, a Doppler detector, a M-mode detector, a spectral Doppler detector, or other detector for ultrasound data. For example, B-mode detectors detect the intensity of an envelope of the received signal and log compress the resulting information. As another example, a color flow or Doppler detector detects velocity, energy associated with frequency shifts or signals indicative of movement or variance. The Doppler detector includes a clutter filter for isolating information associated with slowly or fast moving objects, such as distinguishing between moving tissue and moving fluid. As yet another example, a M-mode detector detects the intensity or magnitude of an envelope signals along a line as a function of time. As yet another example, a spectral Doppler detector detects the velocity, energy and variance of any movement at a particular spatial location as a function of time. Other detectors now known or later developed may be used, such as detectors of a loss of correlation between transmitted pulses, strain rate, strain, or other detectable information from a single signal or a series of signals.

The display 20 comprises a CRT, monitor, LCD, flat screen or other display for displaying an ultrasound image or a sequence of ultrasound images, including an ultrasound image based on information received in response to transmission of unsustainably high transmit powers. For example, the display 20 displays a two-dimensional B-mode image generated based on unsustainably high transmit power pulses. Subsequent B-mode images are also generated sequentially based on standard, lower or other sustainable transmit power pulses. In other embodiments, Doppler or color flow information is provided in addition to the B-mode image and is responsive to either of the sustainable or the unsustainable transmit power pulses. Other images associated with the other various detections and modes of imaging discussed herein may be provided.

Figure 3:
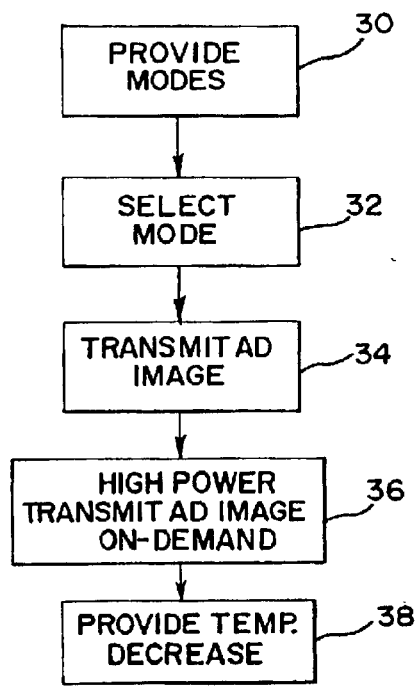
FIG. 3 is a flow diagram of one embodiment of a method for improving ultrasound image quality.

FIG. 3 shows one embodiment of a flow diagram of a method for improving ultrasound image quality. The method uses unsustainable high transmit power pulses in any one or more of various imaging modes. Better penetration and signal-to-noise ratios are provided by delivering a significantly higher amount of acoustic power through the transducer and into the tissues to be imaged. Images associated with a same depth at sustainable transmit pulses may be generated at a higher frequency for better resolution using unsustainably high transmit powers. By recording data responsive to transmit pulses with unsustainably high transmit powers, the user may adjust various parameters and regenerate the image. By providing a memory for storing the data early within the receive processing path, such as at the receiving beamformer 16, the number of parameters for subsequent adjusting offline is increased.

In act 30 of FIG. 3, transmission of pulses having unsustainable power and generation of images based on echoes responsive to the transmission are made available to the user for one, two, or more modes of ultrasound imaging. For example, at least two, three or all modes of ultrasound imaging are provided with an option for unsustainable imaging. Using various menu selections or preset functions on the system 10, the user selects one or more of the modes of ultrasound imaging, such as selecting B-mode imaging or B-mode and Doppler combination imaging. The unsustainably high transmit powers are provided as a selection within the selected mode of imaging or as a separate menu structure providing various modes of imaging. For example, the system 10 is configured to image using sustainable transmit power pulses in one mode of imaging, and a different or same mode of imaging is selected for imaging using unsustainably high transmit power pulses. By providing the unsustainably high transmit power pulses for various modes of imaging, different diagnostic procedures or medical applications may benefit from the image improvements provided by higher transmit powers. A mode of imaging using only unsustainably high transmit powers may also be selected in one embodiment.

In act 32, one of the available modes of imaging is selected for using the unsustainably high transmit power pulses. The method allows for automatic or manual optimization of parameters for both sustainable and unsustainable transmit powers, such as allowing configuration in either transmit pulses using now known or later developed configuration menus or application specific selections. For example, preset parameters that vary as a function of application or imaging mode are provided.

In one embodiment, the system 10 begins imaging using pulses having a sustainable power. The user orients the transducer 14 and may adjust any of various imaging parameters to image a region for diagnosis in act 34.

In act 36, pulses having unsustainably high power are transmitted and an image is generated in response to echoes from the pulses. The unsustainable power is selected based on thermal dose, such as selecting the power and associated time period. The pulses having an unsustainable power are transmitted such that increased tissue heating occurs over a limited period of time to avoid damage to the tissue. For example, pulses with a power resulting in an equilibrium state of 50° C. temperature on skin or internal tissue if maintained for a long period of time (e.g., 15 or 30 minutes or an period time sufficient for a complete ultrasound examination) are transmitted for 4 seconds with a temperature rise to 41° C. As another example, pulses with a power resulting in an equilibrium state of 80° C. temperature on skin or internal tissue if maintained for a long period of time (e.g., 30 minutes) are transmitted for 4 seconds with a temperature rise to 50° C. at the end of 4 seconds. As another example, pulses with a transmit power associated with a 48° C. temperature are transmitted for 16 seconds or less. As yet another example, pulses associated with a temperature of 46° C. if maintained are transmitted for one minute or less. As yet another example, pulses associated with a temperature of 46° C. if maintained are transmitted for 10 seconds with interim pauses or sustainable imaging and then repeated six or fewer times for a total transmission of 1 minute or less. As yet another example, multiple pulses associated with different temperatures are transmitted such that the sum of the durations of the one or more periods of high power pulses is limited by the total thermal dose delivered by all of the high power pulses. 43° C. or other sustainable temperature may be exceeded, but for a limited duration (e.g. to avoid a thermal dose that may cause destruction).

Where the mechanical index (MI) or the voltage limitations of the system 10 may prevent increases in power through voltage, longer transmit pulses, such as a coded excitation pulse, are used. Increasing power either through voltage or pulse length may be limited by the thermal dose to skin or internal tissue.

In act 36, an image is generated in response to echoes from the pulses having unsustainably high power. The image is a B-mode image, a B-mode image responsive to harmonic frequency bands of this fundamental transmit frequency or images of another imaging mode. A B-mode and color flow combination image is generated in one embodiment where both or just one of the portions of the image responsive to the B-mode detection or color flow detection are based on transmit pulses having an unsustainably high power.

The high power transmission and resulting imaging of act 36 are responsive to triggering in one embodiment. A user initiated trigger is provided for on demand image improvement. For example, a user presses a button to initiate transmitting higher power pulses on-demand. As another example, external equipment provides a trigger, such as a signal based on a physiological cycle. For example, an ECG monitor outputs a signal representing the heart cycle or a trigger signal based on a particular portion of the heart cycle. In response to the trigger or after a certain number of trigger signals, the system 10 triggers transmission and imaging using the unsustainably high power pulses. A time period or other system trigger may also be used.

The sustainable and unsustainable pulses are temporally interleaved in one embodiment. For example, sustainable pulses are provided before, after or both before and after transmissions of pulses having high unsustainable power. The higher power pulses are performed for a limited time period, such as for one or two entire heart cycles for cardiac imaging. As discussed above, the time period is a function of the temperature increase caused by the unsustainably high power pulses. The time period of both the transmission of the pulses and the amount of time for the tissue or transducer to cool after transmission of the unsustainably high transmit power pulses ceases is considered in the time-tissue relationship to avoid thermal damage to tissue. A time period at or close to (e.g., within millisecond, seconds or otherwise within 10% of the allowable maximum thermal dose avoiding tissue damage) the maximum thermal dose that avoids temperature related damage to tissue from unsustainably high transmit powers is used. In alternative embodiments, the duration of the use of the unsustainably high transmit power pulses is much less than the time based on the thermal dose or non-linear time-temperature relationship (e.g., more than 10% less than the allowable thermal dose). The thermal dose maximum is based on one or both of tissue and transducer temperature.

In one embodiment, the duration of transmission of unsustainable transmit power is independent of any sustainable transmissions. For example, the duration is set to avoid tissue damage based on the amount of power, the tissue in the imaged region or other characteristics free of a ratio, average or other functional consideration of a duration, power or other characteristic of sustainable transmission times. The duration is set based on the thermal dose applied to the tissue by the unsustainable transmissions independent of other transmissions. Sustainable transmissions are not used, used before, used after or interleaved with unsustainable transmissions. Alternatively, the duration, power or other characteristic of sustainable pulses is used as part of the determination of the duration of the unsustainable pulses.

In other embodiments, the duration as a function of the time-temperature relationship is based on a power dose less than a power dose maximum where the power dose maximum avoids unacceptable tissue damage. The power dose is a function of the power transmitted and the duration of transmission. The temperature response in tissue due to the intensity of an ultrasonic pulse is not instantaneous. Upon initiating a specific intensity by applying the corresponding power to the transducer, the acoustic wave propagates at the speed of sound from the transducer to the tissue. For a constant power acoustic transmission, the tissue heats over time until it reaches a steady state temperature. The time constant and steady state temperature for a specific tissue can be measured for any constant acoustic transmission. This relationship between temperature and power of an acoustic transmission can be tabulated and the time-power relationship can be used to govern pulse duration rather than the time-temperature relationship. For example, pulses with power 12 dB above constant or sustainable acoustic power for 3 seconds provide a power dosage that is unsustainable but result in an elevated peak temperature of 2 degree only for a time period that avoids tissue damage. Other non-temperature relationships of power and tissue damage may limit or be used to determine a power dose that avoids tissue damage. One advantage to the time-power relationship is that, since it can be tabulated for any specific acoustic wave, additional behavior can be included in the tabulation. For example, tissue structures become unstable beyond some power threshold (this threshold being dependent on the specific tissue) and this information can be included in the time-power relationship independent of temperature. The time-power relationship can include any additional pulse shape or frequency dependent information related to tissue damage so that those situations can be readily avoided.

Data responsive to the higher power transmit pulses are used to generate an image on the display 20 and/or stored in a CINE or other memory for later review or for statically generating an image display for a period of time.

Additionally or alternatively, the unsustainable power pulses are interleaved spatially with the sustainable power pulses. The spatial interleaving may increase the amount of time for which the unsustainably high power pulses may be used, but at a reduction in the spatial extent of the improvements associated with the higher power transmissions. The regions for unsustainable and sustainable pulses may vary as a function of time and may overlap. For example, the unsustainably high power pulses are provided for a two-dimensional region of interest or within a three-dimensional sub-volume (e.g. using unsustainably high power pulses for color flow imaging within a region of interest within a B-mode image). The sustainable transmit pulses are used elsewhere within the region of interest, such as for a remainder of the scan region or volume.

In act 38, a decrease in temperature is provided to avoid tissue damage. Ultrasonic pulses having sustainable power are transmitted, allowing the temperature to decrease to a sustainable temperature level, such as 43° C. degrees or less. In one embodiment, transmit pulses having a lower power, such as associated with a 40° C. or less sustainable temperature, are transmitted to allow for a more rapid decrease in temperature after transmission of pulses having an unsustainable power level. These lower power sustainable pulses are transmitted continuously, or the transmit power is adjusted to a higher, but sustainable, transmit power after a period of time. Images in any of various modes may be generated in response to the sustainable power transmit pulses. In alternative embodiments, ultrasound transmissions are ceased for a time period after transmission of pulses having an unsustainable power. For example, all transmissions are ceased for a duration greater than a frame rate associated with imaging from unsustainable power pulses or longer. The duration is a function of the time-temperature relationship, avoiding tissue damage. Ceasing transmission maximizes the rate of temperature reduction to a sustainable temperature level. Maximizing the rate of decrease in temperature allows for an increased time period of imaging with unsustainably high transmit power pulses. Any of various time periods for ceasing or using lower power transmit pulses may be used, such as for seconds (e.g. 5 or 45 seconds) or minutes (e.g. 1 or 2 minutes).

Removing the transducer after short time application of increased of power and subsequent ceasing transmission significantly speeds-up the transducer cooling and shortens patient exposure to higher than 43° C. temperatures. Application of fresh ultrasound gel on the transducer surface prior to reapplication of transducer and continuation of imaging shortens the transducer cooling period even more. These additional steps could be guided by system software (SW), by sound and/or screen messages.

In order to prevent operator errors these steps should be monitored by the ultrasound system. These procedure steps may be monitored by building-in a thermocouple or thermistor into the transducer 14 and monitoring temperature on the transducer surface. Another more general but less accurate approach is using image/signal recognition software. This software determines whether the transducer 14 is on the patient or in air. This software also determines whether fresh gel has been applied on the transducer surface or whether a standoff is in front of transducer. If errors in procedure are detected, the system 10 warns the operator by sound and/or by a message on the screen. If an error repeats, the system 10 prolongs the cooling time and/or limits the number of allowable applications of unsustainable power levels. This software should also prevent firing unsustainable levels of power if the transducer 14 is not applied on the patient with gel on the transducer surface. Application of unsustainable power with the transducer 14 in air and without gel may be dangerous to the patient's skin or to the transducer 14 since temperature jumps without gel and in air are much higher.

One or more images are acquired in response to the transmit pulses with unsustainably high powers. By imaging with sustainable powers prior to acquiring the improved images, the transducer 14 is positioned relative to the patient. Imaging after the unsustainable images are acquired allows for continued monitoring of the region of interest and eventual acquisition of additional improved images associated with unsustainably high powers. During the cooling off time period, such as associated with ceasing ultrasound transmissions, one or more of the images acquired with unsustainably high power transmit pulses are continuously displayed. The improved penetration, signal-to-noise ratio, resolution or other characteristic may assist in diagnosis and is presented to the user during this time period for determination of whether further improved images should be later acquired.

In one embodiment, different sets of unsustainable transmit pulses are transmitted and used for imaging. Each set has a different power. For example, one set of pulses has a high power used for a short time. A second set has an lower, but unsustainable, power used for a longer period of time. The two sets of pulses are used consecutively in any order or may be spaced apart in time by a period of no transmissions or transmission of sustainable pulses. The images responsive to either of the unsustainable sets of pulses are persisted for diagnosis. The different power unsustainable pulses are used in a same imaging session, such as during an ultrasound examination of a patient during a single visit or using a same system configuration of modes.

While the invention has been described above by reference to various embodiments, it should be understood that many changes and modifications can be made without departing from the scope of the invention. For example, pulses having an unsustainably high transmit power may be provided which do not exceed either new or current diagnostic ultrasound imaging FDA, IEC, UL or other safety-standards organizations regulations.

It is therefore intended that the foregoing detailed description be understood as an illustration of the presently preferred embodiments of the invention, and not as a definition of the invention. It is only the following claims, including all equivalents, that are intended to define the scope of the invention.

What is claimed is:

1. A method for ultrasound imaging with improved images, the method comprising:
   (a) transmitting a first set of ultrasonic pulses over a duration, the first set of ultrasonic pulses having an unsustainable power; and
   (b) generating images in response to echoes from the ultrasonic pulses;
   wherein a duration of (a) is a function of a time-tissue temperature relationship and is independent of any sustainable transmissions, the duration operable to avoid a thermal dose from the first set of ultrasound pulses that may cause destruction of tissue.

2. The method of claim 1 wherein the duration is less than a maximum duration based on the time-tissue temperature relationship.

3. The method of claim 2 wherein the duration is within 10% of the maximum duration.

4. The method of claim 2 wherein the duration is less than 90% of the maximum duration.

5. The method of claim 1 wherein the time-tissue temperature relationship comprises an exponential relationship.

6. The method of claim 1 further comprising:
(c) determining the presence of one of gel and a standoff on a transducer; and
(d) indicating an error where the one of the gel and the standoff is absent.

7. The method of claim 1 further comprising:
(c) determining whether a transducer is positioned adjacent the patient; and
(d) preventing (a) where the transducer is spaced from the patient.

8. The method of claim 1 wherein (b) comprises generating images of an imaging mode selected from the group of: B-mode, Doppler mode, color flow mode, harmonic mode, M-mode, three-dimensional mode, four-dimensional mode, extended field of view mode, acoustic streaming mode, acoustic radiation force imaging mode, strain mode and stress echo mode.

9. The method of claim 1 wherein the duration is responsive to the first set of unsustainable pulses being from multiple discontinuous time periods.

10. A method for ultrasound imaging with improved images, the method comprising:
(a) transmitting a first set of ultrasonic pulses over a duration, the first set of ultrasonic pulses having an unsustainable power; and
(b) generating images in response to echoes from the ultrasonic pulses;
wherein a duration of (a) is a function of a time-tissue temperature relationship and is independent of any sustainable transmissions;
wherein the duration provides a thermal dose less than a thermal dose maximum within a scanned region, the thermal dose maximum avoiding tissue damage within the scanned region.

11. The method of claim 10 wherein the thermal dose maximum is a function of a tissue type being imaged.

12. A method for ultrasound imaging with improved images, the method comprising:
(a) transmitting a first set of ultrasonic pulses over a duration, the first set of ultrasonic pulses having an unsustainable power; and
(b) generating images in response to echoes from the ultrasonic pulses;
wherein a duration of (a) is a function of a time-tissue temperature relationship and is independent of any sustainable transmissions;
wherein the duration provides a power dose less than a power dose maximum, the power dose maximum avoiding tissue damage within a scanned region.

13. A method for temporarily improving ultrasound image quality, the method comprising:
(a) transmitting a first set of ultrasonic pulses having a sustainable power; and
(b) transmitting a second set of ultrasonic pulses having an unsustainable power, the unsustainable power unsustainable due to one of tissue temperature and probe temperature;
(c) generating an image in response to echoes from the second set of ultrasonic pulses;
(d) making (a) and (b) available for each of at least two modes of ultrasound imaging, one of the at least two modes of ultrasound imaging comprising a mode other than a color flow mode.

14. The method of claim 13 wherein (a) is performed prior to (b); and further comprising
(e) transmitting a third set of ultrasonic pulses having an sustainable power following (a) and (b) and
(f) generating images in response to echoes from the first and third sets of ultrasonic pulses.

15. The method of claim 13 further comprising:
(e) ceasing any transmission after (b) for a duration greater than a frame rate associated with (b).

16. The method of claim 13 further comprising:
(e) triggering (b).

17. The method of claim 16 wherein (e) comprises performing (b) in response to a user initiated trigger.

18. The method of claim 16 wherein (e) comprises performing (b) in response to a signal based on a physiological signal.

19. The method of claim 16 wherein (e) comprises performing (b) in response to a time period of (b).

20. The method of claim 13 wherein (b) comprises transmitting the second set of ultrasonic pulses having an unsustainable power such that excessive unsustainable tissue heating occurs over a limited period of time.

21. The method of claim 13 wherein (c) comprises generating a B-mode image in response to the second set of pulses.

22. The method of claim 21 wherein (c) comprises generating a harmonic B-mode image, the harmonic being a harmonic of a fundamental frequency of the second set of pulses.

23. The method of claim 22 wherein (b) comprises transmitting the second set of pulses into a target substantially free of added contrast agent during an entire imaging session.

24. The method of claim 13 wherein (b) is performed for at least two entire heart cycles.

25. The method of claim 13 wherein (b) is performed for a first region and (a) is performed for a second region different than the first region.

26. The method of claim 13 wherein (d) comprises making (a) and (b) available for each of at least three modes of ultrasound imaging; and
further comprising:
(e) providing for user selection of one of the at least three modes of ultrasound imaging to be used for (b).

27. A method for ultrasound imaging, the method comprising:
(a) transmitting a first set of ultrasonic pulses having a sustainable power; and
(b) generating a B-mode image in response to echoes from the first set of ultrasonic pulses;
(c) transmitting a second set of ultrasonic pulses having an unsustainable power with a duration operable to avoid tissue damage within an entire imaged region; and
(d) generating a B-mode image in response to echoes from the second set of ultrasonic pulses.

28. The method of claim 27 wherein (d) comprises generating a second harmonic image, the second harmonic relative to a fundamental frequency of the transmitted second set of ultrasonic pulses.

29. A system for ultrasound imaging, the system comprising:
a user interface operable to make unsustainable imaging available;
a transmitter operable to generate a first set of ultrasonic pulses having a sustainable power and operable to generate a second set of ultrasonic pulses having an unsustainable power, the transmitter responsive to a selection of unsustainable imaging for one of at least two modes of ultrasonic imaging, the at least two modes of ultrasound imaging including at least one mode other than color flow, the unsustainable imaging being available for each of the at least two modes of ultrasound imaging; and a display operable to display an image in response to echoes from the second set of ultrasonic pulses.

30. The system of claim 29 further comprising:

a B-mode detector;

wherein the image comprises a two-dimensional B-mode image and the display is operable to display additional B-mode images in response to echoes from the first set of ultrasonic pulses.

31. The system of claim 29 further comprising:

a transducer connected with the transmitter, the transducer having an off-set operable to space the transducer away from a patient's skin and operable to thermally insulate the transducer from the patient's skin.

32. A method for ultrasound imaging, the method comprising:

(a) transmitting a first set of ultrasonic pulses over a duration, the first set of ultrasonic pulses having an unsustainable power; and (b) generating images in response to echoes from the ultrasonic pulses; wherein the duration of (a) is a function of a time-power relationship adapted to avoid any tissue damage within a scanned region.

33. The method of claim 32 wherein the duration is a function of the time-power relationship adapted to avoid mechanical bio-effects.

34. The method of claim 32 wherein the duration is a function of the time-power relationship adapted to avoid thermal bio-effects.

35. A method for ultrasound imaging, the method comprising:

(a) transmitting a first set of ultrasonic pulses over a duration, the first set of ultrasonic pulses having an unsustainable power; and (b) generating images in response to echoes from the first set of ultrasonic pulses;

wherein a duration of (a) is a non-linear function of a time-tissue temperature relationship.

36. The method of claim 35 further comprising:

(c) transmitting a second set of ultrasonic pulses, the second set of ultrasonic pulses having a sustainable power; and (d) generating additional imagines in response to echoes from the second set of ultrasonic pulses, a duration of (a) being independent of a duration of (c).

37. A method for ultrasound imaging, the method comprising:

(a) transmitting a first set of ultrasonic pulses, the first set of ultrasonic pulses having an unsustainable power;

(b) generating a first image in response to echoes from the first set of ultrasonic pulses;

(c) transmitting a second set of ultrasonic pulses, the second set of ultrasonic pulses having an unsustainable power different than the unsustainable power of the first set; and (d) generating a second image in response to echoes from the second set of ultrasonic pulses;

wherein (a) and (b) are performed in a same imaging session.

38. The method of claim 37 further comprising:

(e) transmitting a third set of ultrasonic pulses during the imaging session, the third set of ultrasonic pulses having a sustainable power.

39. The method of claim 38 wherein the first image is for a smaller region than the second image.

40. A method for ultrasound imaging, the method comprising:

(a) transmitting a first set of ultrasonic pulses over a duration, the first set of ultrasonic pulses having an unsustainable power;

(b) transmitting a second set of ultrasonic pulses; and (c) generating images in response to echoes from the second set of ultrasonic pulses, the images free of echoes directly responsive to (a);

wherein the duration of (a) is a function of a time-power relationship adapted to avoid tissue damage anywhere within a region scanned by the first set of ultrasonic pulses.

41. The method of claim 40 wherein the duration is a function of the time-power relationship adapted to avoid mechanical bio-effects.

42. The method of claim 40 wherein the duration is a function of the time-power relationship adapted to avoid thermal bio-effects.

43. A method for ultrasound imaging with improved images, the method comprising:

(a) transmitting a first set of ultrasonic pulses over a duration, the first set of ultrasonic pulses having an unsustainable power; and (b) generating images in response to echoes from the ultrasonic pulses;

wherein a duration of (a) is a function of a time-tissue temperature relationship and is independent of any sustainable transmissions; and wherein (a) and (b) are performed as part of an imaging mode of operation.

44. A method for ultrasound imaging with improved images, the method comprising:

(a) transmitting a first set of ultrasonic pulses over a duration, the first set of ultrasonic pulses having an unsustainable power; and (b) generating images in response to echoes from the ultrasonic pulses;

wherein a duration of (a) is a function of a time-tissue temperature relationship and is independent of any sustainable transmissions, the duration operable to avoid damage to a transducer.

45. A method for ultrasound imaging with improved images, the method comprising:

(a) transmitting a first set of ultrasonic pulses over a duration, the first set of ultrasonic pulses having an unsustainable power; and (b) generating images in response to echoes from the ultrasonic pulses;

wherein a duration of (a) is a function of a time-tissue temperature relationship and is independent of any sustainable transmissions, the duration operable to avoid damage to skin.

* * * * *